US006215036B1

(12) United States Patent
Dorbon et al.

(10) Patent No.: US 6,215,036 B1
(45) Date of Patent: Apr. 10, 2001

(54) METHOD FOR PRODUCING HIGH PURITY ISOBUTYLENE FROM A BUTANE PLUS FRACTION CONTAINING ISOBUTYLENE AND BUTYLENE-1

(75) Inventors: Michel Dorbon, Paris; Blaise Didillon, Rueil Malmaison; Jean-Charles Viltard, Vienne; Jean Cosyns, Maule; Charles Cameron, Paris, all of (FR); Heinz Unterberg, Dormagen; Günter Schümmer, Pullheim, both of (DE); William Brown, Ontario (CA)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/242,058
(22) PCT Filed: Dec. 27, 1996
(86) PCT No.: PCT/FR96/02086
  § 371 Date: Sep. 27, 1999
  § 102(e) Date: Sep. 27, 1999
(87) PCT Pub. No.: WO98/06684
  PCT Pub. Date: Feb. 19, 1998

(30) Foreign Application Priority Data

Aug. 8, 1996 (FR) .................................................. 96 10101

(51) Int. Cl.$^7$ ...................................................... C07C 5/13
(52) U.S. Cl. .......................... 585/664; 585/668; 585/670
(58) Field of Search .................................... 585/664, 668, 585/670

(56) References Cited

U.S. PATENT DOCUMENTS

| 4,104,321 | * | 8/1978 | Word . |
|---|---|---|---|
| 4,132,745 | * | 1/1979 | Amigues . |
| 4,410,754 | * | 10/1983 | Gewartowski . |
| 4,435,609 | * | 3/1984 | Gschwendtner . |
| 4,777,322 | * | 10/1988 | Hoelderich et al. . |
| 5,087,780 | | 2/1992 | Arganbright . |
| 5,130,102 | * | 7/1992 | Jones, Jr. . |
| 5,368,691 | * | 11/1994 | Asselineau et al. . |
| 5,969,203 | * | 10/1999 | Dorbon et al. . |
| 6,054,630 | * | 4/2000 | Mikitenko et al. . |

FOREIGN PATENT DOCUMENTS

| 0170182 | 5/1986 | (EP) . |
|---|---|---|
| 0380374A | 1/1990 | (EP) . |
| 2528033A | 9/1983 | (FR) . |

* cited by examiner

Primary Examiner—Jerry D. Johnson
(74) Attorney, Agent, or Firm—Millen, White, Zelano & Branigan, P.C.

(57) ABSTRACT

A process for processing a feedstock comprising a major amount of olefinic hydrocarbons having 4 carbon atoms per molecule, including isobutene as well as but-1-ene and but-2-enes, wherein the process comprises processing said feedstock in a distillation zone associated with a hydroisomerization reaction zone located at least partly external to the distillation zone, said processing comprising drawing at the height of a draw-off level of the distillation zone at least part of the liquid flowing in the distillation zone, passing said liquid into the external hydroisomerization reaction zone to form a hydroisomerized effluent, and reintroducing at least part of the effluent from said reaction zone reintroduced into the distillation zone at one or more reintroduction level(s), so as to ensure the continuity of the distillation.

14 Claims, 1 Drawing Sheet

METHOD FOR PRODUCING HIGH PURITY ISOBUTYLENE FROM A BUTANE PLUS FRACTION CONTAINING ISOBUTYLENE AND BUTYLENE-1

FIELD OF THE INVENTION

The invention relates to a process for processing a hydrocarbon cut containing essentially olefinic hydrocarbons having 4 carbon atoms per molecule and containing isobutene as well as but-1-ene and but-2-enes in a ratio corresponding substantially to thermodynamic equilibrium, said process comprising passing said cut into a distillation zone associated with a hydroisomerization reaction zone, said process being characterized in that the hydroisomerization zone is at least partly external to the distillation zone. A process of this kind permits the production of high-purity isobutene.

BACKGROUND OF THE INVENTION

Isobutene intended for polymerization must have a purity level above 99% and it must only contain traces of but-1-ene and but-2-enes (a few hundred parts per million by weight, ppm). In fact, if the impurities of isobutene are too high, the resulting polymers are less good in quality and the polymerization yield is lower. As a result it is necessary to remove from a hydrocarbon cut containing isobutene other olefinic hydrocarbons containing 4 carbon atoms per molecule. Since but-1-ene and isobutene have very close boiling points, they cannot be separated by distillation, unless considerable means are used. The other olefinic hydrocarbons having 4 carbon atoms per molecule can be separated from isobutene by distillation.

The main problem that arises when producing high-purity isobutene is thus the separation of but-1-ene from isobutene. Several ways can be contemplated to carry out this separation.

The first way consists of sulfuric acid extraction: the isobutene is selectively hydrated and thereafter regenerated by treatment of the aqueous phase. If the temperature and the concentration are properly controlled, this process results in isobutene of good purity. However, the yield does not usually exceed 90% as extraction is not complete, and dimers and oligomers are formed, leading to the formation of toxic acid sludge.

The second way consists of cracking methyl tert-butyl ether (MTBE): the isobutene is extracted from the $C_4$ cut by reaction with methanol in order to form MTBE. The MTBE is then cracked into methanol and isobutene on an acid catalyst. The recovery yield is generally 96%. The isobutene produced exhibits good purity but the dimethyl ether that may form during cracking has to be removed.

The third way that may be contemplated is the dehydration of tert-butyl alcohol (TBA). Methanol in the above process is replaced by water, and this leads to the formation of TBA. The isobutene is thereafter recovered by dehydration of the TBA. This way is not used commercially, mainly because TBA is very closely connected with the propylene oxide market. TBA can, depending on the processes, be a by-product of propylene oxide.

U.S. Pat. No. 5,177,283 describes a hydrocarbon conversion process comprising passing the feedstock into a fractionation zone, the top effluent being rich in one of the reactants and the bottom effluent being rich in reaction product, said process being such that a liquid flow is subjected to a side-stream draw-off, passed with a hydrogen-rich gaseous flow into a catalytic reaction zone, which gives rise to a reaction zone effluent comprising one of the reactants and the reaction product, a fraction of the gaseous part of said effluent being recycled to the reaction zone, the liquid part of said effluent being fed back into the fractionation zone, generally close to the point where it was drawn off. The hydroisomerization reaction of but-1-ene into but-2-enes is not mentioned.

SUMMARY OF THE INVENTION

The process according to the invention allows a high-purity isobutene to be produced at a low cost and with an excellent yield from an olefinic $C_4$ cut containing at least isobutene as well as but-1-ene and but-2-enes in a ratio corresponding substantially to thermodynamic equilibrium, generally obtained from a steam cracking process, such as the raw $C_4$ cut or 1-raffinate (obtained after butadiene extraction from the raw cut), or from a catalytic cracking process. The process according to the invention is characterized by the integration of distillation and hydroisomerization operations which are arranged and carried out so as to minimize the investment cost of the process, to maximize the conversion of but-1-ene into but-2-enes and to minimize the hydrogenation of isobutene into isobutane, in order to maximize the isobutene yield. Thus, the process according to the invention can also provide at least partially the selective hydrogenation of some polyunsaturated compounds which are most frequently diene-containing or acetyl-containing, such as butadiene, vinylacetylene, methylacetylene and ethylacetylene, when such compounds are present in the feedstock, and the hydroisomerization of but-1-ene into but-2-enes (cis and trans). The but-2-ene products of this hydrogenation operation and of this hydroisomerization operation can then be separated from the isobutene by distillation, unlike but-1-ene. Compared to the other processes mentioned above, the process according to the invention has the advantage of a high isobutene yield, generally above 90%, preferably above 95% and more preferably above 98%, and of producing no oxygen-containing by-products.

The process according to the invention relates to the processing of a feedstock comprising mainly olefinic hydrocarbons having 4 carbon atoms per molecule, including isobutene as well as but-1-ene and but-2-enes in a ratio corresponding substantially to thermodynamic equilibrium, wherein said feedstock is processed in a distillation zone, which generally comprises an exhausting section and a stripping section associated with a hydroisomerization reaction zone, said process being characterized in that the hydroisomerization zone is at least partly external to the distillation zone.

The feedstock of the outer part of the reaction zone is generally drawn off at the height of a draw-off level of the distillation zone and represents at least part, preferably the major part, of the reflux liquid flowing in the distillation zone, preferably flowing in the stripping section, and more preferably flowing at an intermediate level of the stripping section, the effluent of reaction zone being at least partly, preferably mostly, reintroduced into the distillation zone at one or more reintroduction level(s), generally located in proximity to the draw-off level, i.e. substantially at the height of or substantially above or substantially below, most often substantially at the height of or substantially above one draw-off level, preferably said draw-off level, that is to say located usually at a distance from said level corresponding to a height in the range of 0 to 4 theoretical plates above or below a draw-off level, more preferably located substantially at the height of or slightly above the draw-off level, so as to ensure the continuation of the distillation. The process according to the invention makes it possible to obtain at the top of the distillation zone an effluent rich in isobutene usually of high purity, and, at the bottom of the distillation zone, effluent depleted in isobutene.

DETAILED DESCRIPTION OF THE INVENTION

The process according to the invention permits high purity isobutenes to be obtained. Any hydroisomerization reaction zone is usually such that any hydroisomerisation reaction is carried out in the presence of a hydroisomerization catalyst and in a gaseous flow comprising, preferably for the most part, hydrogen.

The feedstock which supplies the distillation zone is introduced into said zone usually at least at one level of said zone, preferably mainly at one single level of said zone. Its ratio corresponds substantially to the but-1-ene: but-2-enes thermodynamic equilibrium during introduction. One of the preferred embodiments of the process according to the invention comprises producing said feedstock from a cut comprising, for the major part thereof, olefinic hydrocarbons comprising 4 carbon atoms per molecule by processing said cut in a first hydroisomerisation zone, usually independent of the outer part of the hydroisomerisation reaction zone associated with the distillation zone, the major part of the effluent of said first hydroisomerisation Zone thus acting as main or secondary feedstock which supplies the distillation zone, according to the definitions given hereinafter in the description. If said feedstock comprises polyunsaturated compounds, which are most frequently diene-containing and/or acetylene-containing, said compounds are preferably converted into butenes by the first hydroisomerisation zone prior to introduction into the distillation zone. However, any other technique which permits the production from a cut, a major part of which comprises $C_4$ olefinic hydrocarbons including but-1-ene and isobutene, of a feedstock where the but-1-ene and but-2-enes are in a ratio which corresponds substantially to thermodynamic equilibrium can also be envisaged within the scope of the invention.

The distillation zone generally comprises at least one column provided with internal distillation equipment which may comprise simple plates, multi-weir plates, random packings and stacked packings, as will be known to the man skilled in the art, so that the total overall efficiency is at least equal to five theoretical stages. In cases known to the skilled person, preferably when using a single column, said zone is divided so as to give in fact give rise to at least two columns which, when put end to end, form said zone, i.e. the stripping section, the optional reaction zone and the exhausting section are distributed on the columns.

The first optional hydroisomerization reaction zone, located upstream of the distillation zone, performs at least partial selective hydrogenation of the polyunsaturated compounds which are most often diene-containing, such as butadiene, in addition to the hydroisomerisation of at least part of the but-1-ene into but-2-enes. It usually comprises at least one hydroisomerization catalyst bed, preferably 1 to 4 catalyst bed(s), comprising a hydroisomerization catalyst; in cases where at least two catalyst beds are incorporated in said reaction zone, these two beds are preferably distributed in at least two reactors and in series or in parallel, more preferably in series, e.g., said first reaction zone comprises a single reactor that contains at least one and preferably only one catalyst bed. In a preferred embodiment of the process according to the present invention, said first reaction zone comprises two reactors preferably distributed in series and each comprising at least one and preferably only one catalyst bed. When said reaction zone comprises at least two reactors, at least part of the effluent of at least one of the reactors contained in said first reaction zone is optionally recycled to said zone, usually at the inlet of a reactor, preferably of said reactor, preferably prior to the injection of a gaseous compound containing hydrogen. It is also possible to carry out recycling around said 1st zone itself, that is to say usually at the inlet of the 1st reactor of said zone, preferably prior to the injection of the gaseous compound containing hydrogen; by way of example, at least part of the effluent of the second reactor is recycled to the inlet of the first reactor. This advantageously permits a reduction in the content of polyunsaturated compounds in the effluent of said 1st reaction zone.

The operating conditions of the first hydroisomerisation zone, when it is present, are usually as follows: the catalyst is identical to the catalyst of the hydroisomerisation zone which will be described hereinafter. The pressure is usually between 4 and 40 bar (1 bar=0.1MPa), preferably between 6 and 30 bar. The temperature is usually between 10 and 150° C., preferably between 20 and 100° C. The $H_2$/hydrocarbon molar ratio is usually adjusted in such a way as to produce virtually complete conversion of the polyunsaturated compounds such as butadiene and sufficient isomerisation of but-1-ene into but-2-enes with limited formation of alkanes.

The hydroisomerization reaction zone associated with the distillation zone generally comprises at least one hydroisomerization catalyst bed comprising a hydroisomerization catalyst, preferably 2 to 6 and more preferably 2 to 4 catalyst beds; in cases where at least two catalyst beds are incorporated in said distillation zone, these two beds are preferably separated by at least one internal distillation equipment. Said hydroisomerization reaction zone provides at least part, preferably a major part, of the hydroisomerization of the but-1-ene present in the feedstock into but-2-enes (cis and trans), in such a way that the but-1-ene content of the top effluent of the distillation zone is at most equal to a specified content. Preferably, the process according to the invention is such that the but-1-ene/isobutene molar ratio in the top effluent of the distillation zone is less than $2 \times 10^{-3}$, preferably less than $1 \times 10^{-3}$, and still more preferably less than $5 \times 10^{-4}$.

One of the preferred embodiments of the process according to the invention comprises supplying the distillation zone, in addition to supplying it with the main feedstock, with a so-called secondary feedstock (in relation to the main feedstock) which may, or may not, come from a hydroisomerisation reaction zone such as the first optional hydroisomerisation reaction zone, and which may, or may not, be independent of the supply of main feedstock to the distillation zone. The secondary feedstock is usually a C4 olefinic cut containing at least isobutene as well as but-1-ene and but-2-enes in a ratio corresponding substantially to thermodynamic equilibrium, and usually comes from a steam cracking process, such as the raw $C_4$ cut or the 1-raffinate, or from catalytic cracking; usually and preferably, the secondary feedstock is an olefinic $C_4$ cut which is virtually free of polyunsaturated compounds, and the content therein of but-1-ene is less than the content of but-1-ene in the main feedstock. If there is a high content of unsaturated compounds in the secondary feedstock, said feedstock is preferably processed in a selective hydrogenation zone prior to entering the distillation zone.

When the main feedstock is introduced at one single introduction level, the secondary feedstock is usually introduced into the distillation zone at at least one introduction level, preferably at one single introduction level, said introduction level depending on the composition of said secondary feedstock. Thus, in a first example, the secondary feedstock can be very rich in isobutene and contain less than 1.5 times the but-1-ene that the main feedstock contains, in which case the secondary feedstock is preferably introduced at one single level which is usually located above the introduction level for the main feedstock. Or, in a second example, the secondary feedstock can be virtually free of but-1-ene, in which case the secondary feedstock is preferably introduced at one single level which is usually located below the introduction level of the main feedstock. It is also possible to mix the main feedstock, prior to it entering the distillation zone, with the secondary feedstock.

According to the process of the present invention the hydroisomerization reaction zone associated with the distillation zone is at least partly external to the distillation zone. Usually, the process according to the invention comprises 1 to 6, more preferably 2 to 4 draw-off levels that supply the external part of said hydroisomerization zone. If said external part of said hydroisomerization zone comprises at least two draw-off levels, then a part of the external part of said hydroisomerization zone that is supplied by a given draw-off level usually comprises at least one reactor and preferably a single reactor. If the external part comprises at least two catalyst beds distributed in at least two reactors, said reactors are arranged in series or in parallel, and each of said reactors is supplied by one single draw-off level, preferably associated with one single reintroduction level, said draw-off level being separate from the draw-off level supplying the other reactor(s).

The process according to the invention is usually such that the feedstock of any part of the hydroisomerisation reaction zone associated with the distillation zone, whether it be internal or possibly external, is drawn off from the height of a draw-off level and represents at least part, preferably a major part, of the liquid (reflux) flowing in the distillation zone, preferably flowing in the stripping zone, and still more preferably flowing at an intermediate level of the stripping zone, the effluent of said hydroisomerisation reaction zone being at least partly, preferably for the major part, reintroduced into the distillation zone in such a way as to ensure the continuity of the distillation operation.

The process according to the invention allows large proportion of the but-1-ene to be isomerized into but-2-enes outside the distillation zone, possibly under pressure and/or temperature conditions that are different from those used in the column. Preferably, the temperature at the inlet (respectively the temperature at the outlet) of the draw-off level which supplies a catalyst bed of the part of the hydroisomerization zone associated with the distillation zone, located outside the distillation zone is substantially similar, i.e. the difference is substantially less than 10° C., to the temperature at the height of the draw-off level (respectively of the reintroduction level). Similarly, the hydroisomerization reaction may be advantageously carried out in said part of the reaction zone located outside the distillation zone at a pressure that is higher than the pressure used inside the distillation zone. This pressure increase also gives rise to increased dissolution of the gaseous flow containing hydrogen in the liquid phase containing the but-1-ene to be hydroisomerized.

According to the process of the present invention, for any catalyst bed of the external part of the hydroisomerization zone associated with the distillation zone and for any catalyst bed of the first optional hydroisomerization zone, the flow of the liquid to be hydroisomerized is preferably cocurrent to the gaseous flow comprising hydrogen.

A preferred embodiment of the process according to the invention comprises using the so-called "pump-around" technique, i.e. a loop pumping technique that consists in causing part and preferably most of the liquid (reflux) to go outside the distillation zone by a factor in the range of 0.5 to 1.5, preferably in the range of 0.75 to 1.3, i.e. the flow rate of a catalyst bed of the external part of the hydroisomerization zone associated with the distillation zone, said bed being supplied at a draw-off level by at least part of the liquid effluent (reflux) flowing on a distillation plate associated with said draw-off level (that is to say on which a part of the liquid effluent is drawn off) and by at least part of the liquid corresponding to the recycle to effluent of said bed, substantially below or substantially above or substantially at the same height as said draw-off level, is smaller or greater than once the flow rate of the liquid effluent flowing on said plate, in a more preferably manner equal to once the flow rate of the liquid effluent flowing on said plate, that is to say usually in the same order of magnitude like the flow rate of the liquid effluent flowing on said plate.

Thus flow rate of a reactor of the external part of the hydroisomerization zone associated with the distillation zone, at the draw-off level which feeds said reactor, is in the range of 0.5 to 1.5 time the flow rate of the liquid effluent flowing on said plate, associated to said draw off level.

According to an embodiment of the process according to the invention, the hydroisomerization zone associated with the distillation zone is both partly incorporated in the distillation zone, i.e. internal to the distillation zone, and partly external to the distillation zone. According to such an embodiment, the hydroisomerization zone comprises at least two, preferably at least three catalyst beds, at least one catalyst bed being internal to the distillation zone, and at least one catalyst bed being external to the distillation zone. Preferably, part of or all of the liquid hydrocarbons, including the but-1-ene to be isomerized, first circulate in the external part of said hydroisomerization zone, then in the internal part of said hydroisomerization zone. For the part of the reaction zone internal to the distillation zone, the liquid (reflux) is conveniently drawn off by flowing into the part of the reaction zone internal to the distillation zone, and the liquid is also conveniently reintroduced into the distillation zone by the flow of liquid from the part of the reaction zone internal to the distillation zone. Furthermore, the process according to the invention is preferably such that for any catalyst bed of the part which may be internal to the hydroisomerization zone associated with the distillation zone, the flow of the liquid containing the reactant, but-1-ene, is cocurrent or countercurrent to the flow of the gaseous flow comprising hydrogen, According to another preferred embodiment of the process according to the invention, independently of the first embodiment, the hydroisomerization zone associated with the distillation zone is totally external to the distillation zone. It then has the features of the external part of the hydroisomerization zone associated with the distillation zone of the previous embodiment.

For hydroisomerization according to the process of the invention, the molar ratio of $H_2$ to hydrocarbons entering the reaction zone associated with the distillation zone is at least $10^{-5}$. This molar ratio may be optimized so that, on the one hand, all the hydrogen is consumed in the hydroisomerisation reactors in order to prevent a device for the recovery of hydrogen at the outlet from the reaction zone, and, on the other hand, in order to minimize isobutene hydrogenation side reactions to maximize the isobutene yield of the process, and finally to have enough hydrogen all along the reaction zone for the hydroisomerization reaction of but-1-ene into but-2-enes to occur. However, if the conditions are such that there is excess hydrogen, the excess hydrogen may be advantageously recovered. For example, the excess hydrogen leaving the top of any distillation reaction zone may be recovered, then compressed and re-used in the hydroisomerization reaction zone associated with the distillation zone.

The hydrogen contained in the gaseous flow used in the process of the invention for the hydroisomerization of but-1-ene into but-2-ene, either in the first optional hydroisomerisation zone or in the hydroisomerization zone associated with the distillation zone, usually comes, for the most part, preferably virtually entirely, from outside the distillation zone. It can come from any source producing hydrogen with at least 50% by volume of purity, preferably at least 80% by volume of purity and more preferably at least 90% by volume of purity. Examples include hydrogen from steam cracking, catalytic reforming, PSA (pressure swing adsorption) or electrochemical generation processes.

When the hydroisomerization zone associated with the distillation zone is at least partly incorporated in the distillation zone, the hydroisomerization catalyst can be placed in said incorporated part using any convenient catalytic distillation technology. There are two main types of such technology.

According to the first type, the reaction and the distillation occur simultaneously in the same physical space, as disclosed for example in patent application WO-A-90/02,603, U.S. Pat. Nos. 4,471,154, 4,475,005, 4,215,011, 4,307,254, 4,336,407, 4,439,350, 5,189,001, 5,266,546, 5,073,236, 5,215,011, 5,275,790, 5,338,517, 5,308,592, 5,236,663, 5,338,518, as well as patents EP-B1-0,008,860, EP-B1-0,448,884, EP-B1-0,396,650 and EP-B1-0,494,550 and patent application EP-A1-0,559,511. The catalyst is then preferably in contact with a descending liquid phase, generated by the reflux introduced at the top of the distillation zone, and with an ascending vapour phase generated by the reboiling steam introduced at the bottom of the zone. According to this type of technology, the required gaseous hydrogen flow hydrogen may be admixed with the vapour phase, preferably substantially at the inlet of at least one catalyst bed of the reaction zone.

According to the second type, the catalyst is arranged so that the reaction and the distillation generally occur in an independent and consecutive way, as disclosed for example by U.S. Pat. Nos. 4,847,430, 5,130,102 and 5,368,691, and the distillation vapour substantially does not flow through any catalyst bed of the reaction zone. Thus, if this type of technology is used, the flow of liquid to be hydroisomerized is cocurrent to the hydrogen gaseous, and such that the distillation vapour is substantially not in contact with the catalyst (in practice the vapour is preferably separated from said liquid to be hydroisomerized) for any catalyst bed of the internal part of the hydroisomerization zone. Such systems preferably comprise at least one liquid distribution device, for example, a liquid distributor, in any catalyst bed of the reaction zone. However, since these technologies were designed for catalytic reactions occurring between liquid reactants, they must be modified for a catalytic hydroisomerization reaction for which one of the reactants, hydrogen, is in the gaseous state.

For any catalyst bed of the part which may be internal to the hydroisomerization zone, it is therefore preferable to add a device delivering a gaseous flow comprising hydrogen, for example according to one of the techniques described hereafter. Thus, for any catalyst bed of the hydroisomerization zone internal to the distillation zone, the internal part of the hydroisomerization zone comprises at least one device for distributing liquid usually situated below said catalytic bed, and at least one device for delivering a gaseous flow comprising hydrogen usually situated below or inside said catalytic bed, preferably in that last case in proximity to the device for delivering liquid. According to one technique, the device for delivering a gaseous flow comprising hydrogen in any catalytic bed is identical to the liquid distribution device, i.e. there is a mean for the introduction of the gas in the liquid upstream the device for distributing liquid (according to the way that liquid circulates). In practice and in a usual language, that means that there is a tap of the gas into the liquid, upstream the device for distributing liquid. According to another technique, the device for delivering a gaseous flow comprising hydrogen is placed substantially at the level of the liquid distribution device, the gaseous flow and the liquid being delivered separately into the catalyst bed. According to this other technique, the device for delivering a gaseous flow comprising hydrogen is placed below or within the catalyst bed, preferably in proximity to said device for distributing liquid into said catalyst bed.

Thus, when the hydroisomerization zone associated with the distillation zone is at least partly internal to the distillation zone, a preferred embodiment of the process according to the invention is such that the catalyst of the internal part of said hydroisomerization zone is placed in said part according to the base pattern described in U.S. Pat. No. 5,368,691, and arranged so that any catalyst bed of the internal part of the hydroisomerization zone is supplied by a gaseous flow comprising hydrogen, evenly distributed at the base thereof, for example according to one of the techniques described above. According to this technology, where the distillation zone comprises a single column and the hydroisomerization zone is totally internal to said column (thus differing from the process according to the invention), the catalyst contained in any catalyst bed, internal to the distillation zone, is then in contact with an ascending liquid phase, generated by the reflux introduced at the top of the distillation column, and with the gaseous flow comprising hydrogen that circulates in the same direction as the liquid, contact with the distillation vapour phase being prevented by causing the latter to pass through at least one chimney specially designed for this purpose.

When the hydroisomerization zone associated with the distillation zone is at least partly internal to the distillation zone, the operating conditions of said internal part are linked with the distillation operating conditions. Distillation is preferably conducted so as to minimize the amount of isobutene in the bottom product in order to maximize the isobutene yield of the process and to minimize the amount of but-2-ene and but-1-ene in the top product so as to have high-purity isobutene at the top. It is carried out at a pressure preferably in the range of 2 to 30 bars, preferably in the range of 4 to 15 bars, more preferably in the range of 4 to 10 bar (1 bar=$10^5$ Pa), with preferably a reflux ratio in the range of 1 and 30, more preferably between 5 and 20. The temperature at the top of the distillation zone is preferably in the range of 0 to 200° C., and the temperature at the bottom of the distillation zone is preferably in the range of 5 to 250° C. The temperatures in the distillation zone can be calculated from the pressures given above, as it is well known from the one skilled in the Art. The hydroisomerization reaction is preferably conducted under conditions that are intermediate between those established at the top and at the bottom of the distillation zone, preferably at a temperature in the range of 20 to 150° C., more preferably 40 to 80° C., and preferably at a pressure in the range of 2 to 30 bars, preferably 4 to 15 bar, more preferably in the range of 4 to 10 bar. The liquid subjected to hydroisomerization is supplied by a gaseous flow comprising, preferably for the most part, hydrogen.

In the external part of the hydroisomerization zone associated with the distillation zone, the catalyst is placed in any catalyst bed according to any convenient technology known to the man skilled in the art, under operating conditions (temperature, pressure, etc.) that may be independent or not, preferably independent, of the operating conditions of the distillation zone.

In the part of the hydroisomerization zone associated with the distillation zone external to the distillation zone, the operating conditions are preferably independent of the operating conditions of the distillation zone. They are usually as follows: the pressure required for this hydroisomerization stage is preferably in the range of about 1 to 40 bars abs., more preferably about 2 to 30 bars and even more preferably about 4 to 25 bars. The operating temperature of said external part of said hydroisomerization zone is preferably in the range of about 20 to 150° C., more preferably about 40 to 100° C., and even more preferably about 40 to 80° C. The space velocity in said second hydroisomerization zone, calculated in relation to the catalyst, is preferably in the range of about 1 to 100 and more particularly about 4 to 50 $h^{-1}$ (volume of feed per volume of catalyst and per hour). The corresponding hydrogen flow rate is such that the molar ratio of $H_2$ to hydrocarbons entering the hydroisomerization zone associated with the distillation zone is preferably at least $10^{-5}$. This ratio is most preferably in the range of about $10^{-5}$ to about 3 and even more preferably about $10^{-4}$ to about 1.

More generally, the catalyst used in any hydroisomerization zone according to the process of the present invention preferably comprises at least one metal selected from the group consisting of noble metals of group VIII of the periodic classification of elements and nickel, that is to say, selected from the group formed by ruthenium, rhodium, palladium, osmium, iridium, platinum, preferably palladium or nickel, used as it is or preferably deposited on a support. The metal is preferably in reduced form for at least 50% by weight of its total. When nickel is used, the proportion of nickel in relation to the total weight of catalyst is in the range of 5 to 70%, preferably in the range of 10 to 70%. Furthermore, a catalyst wherein the average size of the nickel crystallites is less than 10 nm, preferably less than 8 nm and most preferably less than 6 nm may preferably be used. However any other hydroisomerization catalyst known to the man skilled in the art may also be selected. The catalyst is usually treated with a sulfur compound, then with hydrogen prior to its use. The catalyst is generally sulfurized in situ or ex situ so that sulfur is chemisorbed on at least part of the metal. The chemisorbed sulfur has the effect of promoting the reaction of hydroisomerization of the but-1-ene into but-2-ene in relation to the reaction of hydrogenation of the isobutene, and therefore of maximizing the isobutene yield of the process.

The support of the hydroisomerisation catalyst is preferably selected from the group consisting of alumina, silica-aluminas, silica, zeolites, activated coal, clays, aluminous cements, rare earth oxides and alkaline earth oxides, alone or in admixture. An alumina-based or a silica-based support is preferably used, with a specific surface in the range of 10 to 300 $m^2/g$, preferably 30 to 70 $m^2/g$.

Non-limitative examples of catalysts that may be used within the scope of the present invention include commercial catalysts such as those sold by the Catalysts and Chemicals company under reference number C-31, by Girdler Corporation under reference number G-55 or preferably by the Procatalyse company under reference numbers LD-265, LD-265S, LD-267 and LD-267R.

Figure 1:
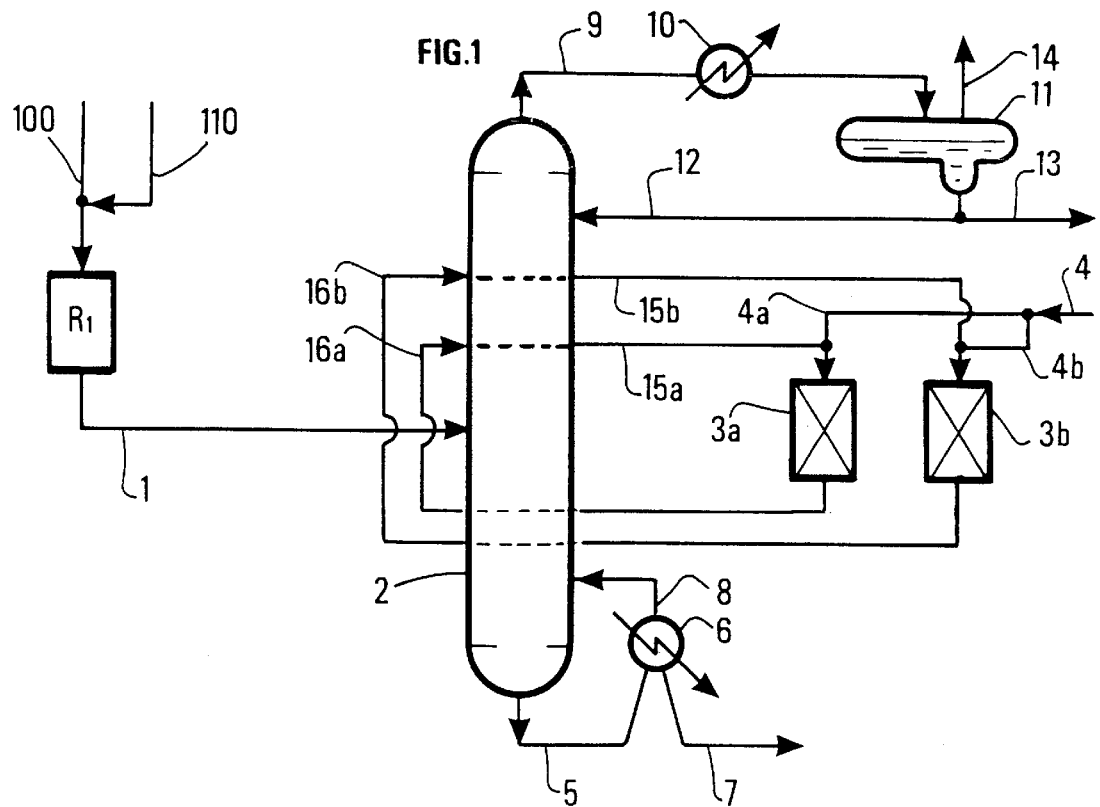
FIGS. 1 and 2 each illustrate a preferred embodiment of the process according to the invention. Similar devices are represented by the same digits in each figure. Equipment such as pumps or valves is not shown.

A first embodiment of the process is shown in FIG. 1. The raw $C_4$ cut, after extraction of the majority of the butadiene (cut called 1-raffinate), and containing at least isobutene and but-1-ene, is fed into a hydroisomerization-hydrogenation reactor R1 through line 100 in admixture with hydrogen fed through line 110. The amount of hydrogen is adjusted particularly as a function of the multi-unsaturated compound content of the feedstock, such as butadiene, vinylacetylene, methylacetylene and ethylacetylene, so as to have a sufficient excess to perform at least partial hydrogenation and hydroisomerization of but-1-ene into but-2-enes. The resulting product at the outlet of reactor R1 is fed through line 1 into column 2. Said column contains internal distillation equipment comprising, for example in the case shown in FIG. 1, plates or packings partly represented by dotted lines in said figure.

In some cases, when the multi-unsaturated compound content of the $C_4$ cut is too high, part of the effluent of reactor R1, after heat exchange, may be recycled to reactor R1 prior to being admixed with hydrogen fed through line 110. Recycling part of the effluent of reactor R1 depleted in polyunsaturated compounds allows the polyunsaturated compounds content of the feedstock of reactor R1 to be reduced. The recycle line and possible associated equipment are not shown in FIG. 1.

At the bottom of the column, the least volatile fraction, mainly consisting of but-2-enes, is recovered through line 5, reboiled in exchanger 6 and discharged through line 7. The reboiling steam is reintroduced into the column through line 8. At the top of the column, the most volatile fraction, i.e. mainly comprising isobutene and isobutane, is fed through line 9 into a condenser 10, then into a drum 11 where a separation is carried out between a liquid phase and a vapour phase containing mainly light hydrocarbons $C_3^-$ and hydrogen, possibly in excess. The vapour phase is discharged out of the drum through line 14. The part of the liquid phase of drum 11 which constitutes the liquid distillate highly depleted in n-butenes is discharged through line 13, while the other part is fed back, through line 12, to the top of the column to ensure the reflux thereof.

By means of a draw-off plate placed in the stripping section of the column, a liquid is drawn off through line 15a and fed to the top of a hydroisomerization reactor 3a, after adding hydrogen through lines 4, then 4a. The effluent from the hydroisomerization reactor is recycled to the column through line 16a, substantially at the level of draw-off line 15a.

Similarly, a liquid is drawn off through line 15b and fed into hydroisomerization reactor 3b after adding hydrogen through lines 4 and 4b, and the effluent from hydroisomerization reactor 3b is recycled to the column through line 16b (very slightly above draw-off level 15b).

Figure 2:
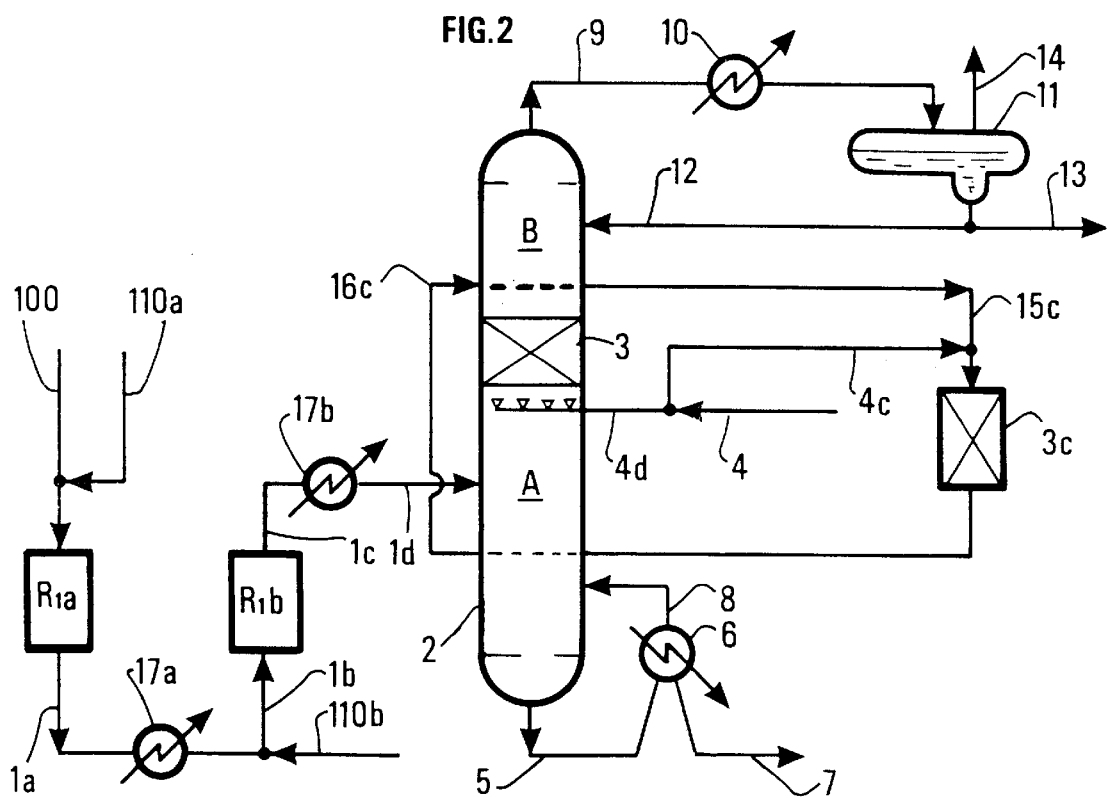

According to a second embodiment of the process, shown in FIG. 2, the raw steam cracking $C_4$ cut is fed into a hydroisomerization-hydrogenation reactor R1a through line 100, in admixture with hydrogen introduced through line 110a. The effluent of reactor R1a is fed into cooling exchanger 17a through line 1a, then into a second hydroisomerization reactor R1b through line 1b, in admixture with hydrogen introduced through line 110b. The effluent of reactor R1b is fed into cooling exchanger 17b through line 1c, then, via line 1d, into a distillation column 2 provided with internal distillation equipment which comprises, for example in the case of FIG. 2, multi-weir distillation plates, as well as an internal catalytic zone 3 containing a hydroisomerization catalyst and supplied with hydrogen through lines 4 and 4d.

In some cases, when the multi-unsaturated compound content of the $C_4$ cut is too high, part of the effluent of reactor R1a, after heat exchange for example in exchanger 17a, may be recycled to reactor R1a prior to receiving hydrogen through line 110a. Recycling part of the effluent of reactor R1a depleted in polyunsaturated compounds allows the polyunsaturated compound content in the feedstock of reactor R1a to be reduced. The recycle line and possible associated equipment is not shown in FIG. 2.

The top and the bottom effluents in the column are processed as described above for the first embodiment of the process. By means of a draw-off plate placed in the stripping section of the column, a liquid is drawn off through line 15c and, after addition of hydrogen through line 4c, fed into hydroisomerization reactor 3c. The effluent of the hydroisomerization reactor is recycled to the distillation column through line 16c, at a level substantially at the same height as the liquid draw-off level 15c.

The examples hereafter illustrate the invention in a non limitative way. Other reactor, exchange arrangements etc., different from those described may of course be contemplated as variants of the invention, provided that they fall within the scope of the present invention..

EXAMPLE 1

The hydroisomerization of a $C_4$ cut and distillation were successively carried out discontinuously. The feedstock was hydroisomerized as a first step. The effluent from this first step was distilled; a first sample of an intermediate draw-off was hydroisomerized. The hydroisomerization effluent, i.e. the sample which is re-injected into the column, was distilled. A sample of this second distillation was hydroisomerized.

The hydroisomerization operations are carried out in a pilot plant equipped with an isothermal reactor. The reactor is filled with 1.51 of catalyst LD-265 sold by Procatalyse. The catalyst is sulfurized and activated in situ according to a procedure recommended by the catalyst supplier.

The distillation operations are carried out in an adiabatic column having an internal diameter of 163 mm and a height of 10 m. The column consists of four 1.78m high beds above the feedstock injection level, filled with a packing commercially available from the Sulzer company under the trade designation M550Y and of two 1 m high beds below the feedstock injection level, filled with Pall rings.

First hydroisomerization

The mean operating conditions during the example are as follows:

Reactor temperature: 80° C.
Reactor pressure: 20 bars
Residence time: 0.25 h
$H_2$/feedstock molar ratio: 3.

Table 1 hereafter shows the compositions of the feedstock and of the effluent of the hydroisomerization reactor working under the conditions described above.

TABLE 1

|  | Feedstock (% by weight) | Effluent (% by weight) |
|---|---|---|
| $<C_4$ | 0.29 | 0.23 |
| $iC_4$ | 2.98 | 3.10 |
| $iC_4^=$ | 44.90 | 44.42 |
| $nC_4^=1$ | 26.95 | 4.26 |
| $C_4^{==}1,3$ | 0.13 | 0.00 |
| $nC_4$ | 11.72 | 14.41 |
| $nC_4^=$ 2 trans | 8.73 | 21.37 |
| Neo $C_5$ | 0.24 | 0.23 |
| Me Cyclo $C_3$ | 0.06 | 0.06 |
| $nC_4^=$ 2 cis | 4.03 | 11.92 |
| $>C_4$ | 0.01 | 0.00 | with the following key for this table and for the following tables:

$<C_4$ compounds with less than 4 (4 excluded) carbon atoms per molecule (or $C_3^-$)
i $C_4$ isobutane
=
i $C_4$ isobutene
=
n $C_4$ 1 but-1-ene
==
$C_4$ 1,3 buta-1,3-diene
n $C_4$ normal butane
=
n $C_4$ 2 trans trans but-2-ene
Neo $C_5$ neopentane (or dimethyl propane)
Me Cyclo $C_3$ methyl cyclopropane
=
n $C_4$ 2 cis cis but-2-ene
$>C_4$ compounds with more than 4 (4 excluded) carbon atoms per molecule (or $C_5^+$)
First distillation The distillation of the effluent of the example presented above was carried out under the following operating conditions:

Column pressure: 4 bars
Reflux ratio (R/D): 20
Feedstock temperature: 33° C.
Temperature at the top of the column: 32° C.
Temperature at the bottom of the column: 63° C.

TABLE 2

|  | Feedstock (% by weight) | Top effluent (% by weight) |
|---|---|---|
| $<C_4$ | 0.23 | 0.44 |
| $iC_4$ | 3.10 | 6.71 |
| $iC_4^=$ | 44.42 | 83.34 |
| $nC_4^=1$ | 4.26 | 7.39 |
| $C_4^{==}1,3$ | 0.00 | 0.00 |
| $nC_4$ | 14.41 | 1.62 |
| $nC_4^=$ 2 trans | 21.37 | 0.44 |
| Neo $C_5$ | 0.23 | — |
| Me Cyclo $C_3$ | 0.06 | — |
| $nC_4^=$ 2 cis | 11.92 | 0.05 |
| $>C_4$ | — | — |

Second hydroisomerization

The mean operating conditions during the test are as follows:

Reactor temperature: 65° C.
Reactor pressure: 20 bars

Residence time: 0.25 h $H_2$/feedstock molar ratio: 0.6.

Table 3 hereafter shows the compositions of the feedstock and of the effluent of the hydroisomerization reactor working under the conditions described above.

TABLE 3

| | Feedstock (% by weight) | Effluent (% by weight) |
|---|---|---|
| <$C_4$ | 0.44 | 0.39 |
| $iC_4$ | 6.71 | 6.91 |
| $iC_4^=$ | 83.34 | 82.95 |
| $nC_4^=1$ | 7.39 | 0.81 |
| $C_4^{==}1,3$ | — | — |
| $nC_4$ | 1.62 | 2.09 |
| $nC_4^=$ 2 trans | 0.44 | 4.44 |
| Neo $C_5$ | — | — |
| Me Cyclo $C_3$ | — | — |
| $nC_4^=$ 2 cis | 0.05 | 2.42 |
| >$C_4$ | — | — |

Second distillation

The distillation of the effluent of the test presented above was carried out under the operating conditions as follows:

Column pressure: 4 bars

Reflux ratio (R/D): 13.5

Feedstock temperature: 36° C.

Temperature at the top of the column: 41° C.

Temperature at the bottom of the column: 55° C.

Table 4 hereafter shows the compositions of the feedstock and of the top effluent of the distillation column working under the conditions described above.

TABLE 4

| | Feedstock (% by weight) | Top effluent (% by weight) |
|---|---|---|
| <$C_4$ | 0.39 | 0.65 |
| $iC_4$ | 6.91 | 13.71 |
| $iC_4^=$ | 82.95 | 84.83 |
| $nC_4^=1$ | 0.81 | 0.51 |
| $C_4^{==}1,3$ | — | — |
| $nC_4$ | 2.09 | 0.14 |
| $nC_4^=$ 2 trans | 4.44 | 0.12 |
| Neo $C_5$ | — | — |
| Me Cyclo $C_3$ | — | — |
| $nC_4^=$ 2 cis | 2.42 | 0.05 |
| >$C_4$ | — | — |

Third hydroisomerization

The mean operating conditions during the test are as follows:

Reactor temperature: 60° C.

Reactor pressure: 20 bars

Residence time: 0.25 to 0.1 h $H_2$/feedstock molar ratio: 1.

Table 5 hereafter shows the compositions of the feedstock and of the effluent of the hydroisomerization reactor working under the conditions described above.

TABLE 5

| | Feedstock (% by weight) | Effluent (% by weight) |
|---|---|---|
| <$C_4$ | 0.65 | 0.565 |
| $iC_4$ | 13.71 | 14.55 |
| $iC_4^=$ | 84.83 | 84.07 |
| $nC_4^=1$ | 0.51 | 0.03 |
| $C_4^{==}1,3$ | — | — |

TABLE 5-continued

| | Feedstock (% by weight) | Effluent (% by weight) |
|---|---|---|
| $nC_4$ | 0.14 | 0.22 |
| $nC_4^=$ 2 trans | 0.12 | 0.38 |
| Neo $C_5$ | — | — |
| Me Cyclo $C_3$ | — | — |
| $nC_4^=$ 2 cis | 0.05 | 0.18 |
| >$C_4$ | — | — |

Third distillation

The distillation of the effluent of the test presented above was carried out with the operating conditions as follows:

Column pressure: 4 bars

Reflux ratio (R/D): 13.5

Feedstock temperature: 36° C.

Temperature at the top of the column: 41° C.

Temperature at the bottom of the column: 55° C.

Table 6 hereafter shows the compositions of the feedstock and of the top effluent of the distillation column working under the conditions described above.

TABLE 6

| | Feedstock (% by weight) | Top effluent (% by weight) |
|---|---|---|
| <$C_4$ | 0.565 | 0.57 |
| $iC_4$ | 14.55 | 14.66 |
| $iC_4^=$ | 84.07 | 84.69 |
| $nC_4^=1$ | 0.03 | 0.03 |
| $C_4^{==}1,3$ | — | — |
| $nC_4$ | 0.22 | 0.01 |
| $nC_4^=$ 2 trans | 0.38 | 0.04 |
| Neo $C_5$ | — | — |
| Me Cyclo $C_3$ | — | — |
| $nC_4^=$ 2 cis | 0.18 | — |
| >$C_4$ | — | — |

These successive and discontinuous hydroisomerization and distillation operations illustrate the operation of separation of but-1-ene from isobutene using a continuous process according to the invention.

EXAMPLE 2

Hydroisomerization was carried out from raffinate-1 on the hydroisomerization catalyst LD-267R commercially available from the Procatalyse company. The results of these tests are shown in Table 7 below; the results allow calculation parameters to be determined which allow the process to be simulated using suitable software. The software used for this simulation is commercially available from the SIMCI company under the trade name Pro2.

TABLE 7

| | | results | | | | | | | | | |
|---|---|---|---|---|---|---|---|---|---|---|---|
| T °C. | | 40 | 60 | 90 | 50 | 50 | 50 | 50 | 50 | 50 | 50 |
| LHSV $h^{-1}$ | | 30 | 30 | 30 | 30 | 30 | 30 | 30 | 30 | 20 | 40 |
| Pbar | | 10 | 10 | 10 | 6.5 | 10 | 15 | 10 | 10 | 10 | 10 |
| $H_2$/HC m/m | | 0.17 | 0.17 | 0.17 | 0.17 | 0.17 | 0.17 | 0.1 | 0.19 | 0.17 | 0.17 |
| | feed | effl | effl | effl | effl | effl | effl | effl | effl | effl | effl |
| $<C_4$ | 0.14 | 0.11 | 0.12 | 0.11 | 0.10 | 0.10 | 0.10 | 0.10 | 0.11 | 0.10 | 0.09 |
| $iC_4$— | 5.69 | 5.75 | 5.75 | 5.73 | 5.71 | 5.76 | 5.75 | 5.72 | 5.76 | 5.75 | 5.74 |
| $iC_4$= | 78.67 | 72.82 | 78.71 | 78.73 | 78.77 | 78.73 | 78.73 | 78.75 | 78.71 | 78.71 | 78.74 |
| 1-$C_4$— | 3.66 | 1.30 | 0.91 | 0.75 | 1.15 | 1.01 | 1.18 | 1.13 | 1.00 | 0.8 | 1.32 |
| n-$C_4$— | 7.16 | 7.19 | 7.17 | 7.14 | 7.14 | 7.18 | 7.19 | 7.16 | 7.20 | 7.19 | 7.18 |
| tr2-$C_4$— | 4.36 | 5.40 | 5.48 | 5.40 | 5.46 | 5.49 | 5.41 | 5.46 | 5.48 | 5.59 | 5.37 |
| cs2-$C_4$ | 0.32 | 1.54 | 1.85 | 2.14 | 1.66 | 1.74 | 1.64 | 1.69 | 1.75 | 1.86 | 1.56 | feed = feedstock and
effl = effluent.

Two simulated examples were carried out. They are described below.

EXAMPLE 2A

The configuration of the plant comprising three hydroisomerization zones outside the column is as follows:
column with 130 theoretical plates, numbered downwards,
feed plate no. 90,
the external reactors are fed through draw-offs respectively at the level of the plates 10, 25 and 39. The effluent of each of the external reactors is reintroduced onto the draw-off plate feeding that external reactor.
Reactors:
The three reactors each contain 7.5 tons of catalyst.
Operating conditions:
Reflux ratio: 12,
pressure at the top of the column: 6.2 bars abs.,
pressure at the bottom of the column: 7 bars abs.,
column feed temperature: 59° C.,
temperature at the top of the column: 45° C.,
temperature at the bottom of the column: 64.5° C.,
temperature of the reactor fed through a draw-off at plate 10: 53° C.,
pressure of the reactor fed through a draw-off at plate 10: 6.6 bars abs.,
flow rate in the reactor fed through a draw-off at plate 10: 2800 kmol/h,
temperature of the reactor fed through a draw-off at plate 25: 54° C.,
pressure of the reactor fed through a draw-off at plate 25: 6.6 bars abs.,
flow rate in the reactor fed through a draw-off at plate 25: 2800 kmol/h,
temperature of the reactor fed through a draw-off at plate 39: 55° C.,
pressure of the reactor fed through a draw-off at plate 39: 6.7 bars abs.,
flow rate in the reactor fed through a draw-off at plate 39: 2800 kmol/h.

With this configuration and under such operating conditions, simulation gave the following results:

| | Column feed (kmol/h) | Column top (kmol/h) | Column bottom (kmol/h) |
|---|---|---|---|
| $<C_4$ | 1.12 | 1.12 | 0.00 |
| $iC_4$ | 4.46 | 5.32 | 0.00 |
| $iC_4$= | 110.08 | 108.32 | 0.89 |
| $nC_4$=1 | 7.53 | 0.03 | 0.19 |
| $nC_4$ | 55.27 | 0.67 | 54.66 |
| $nC_4$= 2 tr | 79.74 | 0.07 | 84.49 |
| $nC_4$= 2 cis | 33.49 | 0.00 | 35.9 |
| $H_2$ | 1.2 | 0.27 | 0.00 |
| Total | 292.88 | 115.81 | 176.14 |

Isobutene yield at the column top: 98.4%
but-1-ene in isobutene at the column top: 266 ppm.

EXAMPLE 2B

The configuration of the plant comprising two hydroisomerization zones inside the column and one hydroisomerization zone outside is as follows:
130 theoretical plates, numbered downwards,
feed plate n° 90,
reactive plates 10 and 25,
the external reactor is fed through a draw-off at the level of plate 39. The effluent of the external reactor is reintroduced onto draw-off plate 39 feeding the external reactor.
Reactors:
The reactor upstream from the column contains 7.5 m³ of catalyst, the reactive plates 10 and 25 and the external reactor contain each 7.5 m³ of catalyst.
Operating conditions:
Reflux ratio: 12,
pressure at the top of the column: 6.2 bars abs.,
pressure at the bottom of the column: 7 bars abs.,
column feed temperature: 59° C.,
temperature at the top of the column: 47.5° C.,
temperature at the bottom of the column: 64.6° C.,
temperature of the reactive plate 10: 53° C.,
pressure of the reactive plate 10: 6.6 bars abs.,
flow rate in the reactive plate 10: 1555 kmol/h,
temperature of the reactive plate 25: 54° C.,
pressure of the reactive plate 25: 6.6 bars abs.,
flow rate in the reactive plate 25: 1558 kmol/h,
temperature of the reactor fed through a draw-off at plate 39: 55° C.,
pressure of the reactor fed through a draw-off at plate 39: 6.7 bars abs., flow rate in the reactor fed through a draw-off at plate 39: 2800 kmol/h.

With this configuration and under such operating conditions, simulation gave the results as follows:

|  | Column feed (kmol/h) | Column top (kmol/h) | Column bottom (kmol/h) |
|---|---|---|---|
| <$C_4$ | 1.12 | 1.12 | 0.00 |
| $iC_4$ | 4.46 | 5.44 | 0.00 |
| $iC_4^=$ | 110.08 | 108.34 | 0.89 |
| $nC_4^=1$ | 7.53 | 0.05 | 0.19 |
| $nC_4$ | 55.27 | 0.90 | 54.35 |
| $nC_4^=$ 2 tr | 79.74 | 0.10 | 84.40 |
| $nC_4^=$ 2 cis | 33.49 | 0.01 | 35.89 |
| $H_2$ | 1.2 | 0.14 | 0.00 |
| Total | 292.88 | 116.1 | 175.73 |

Isobutene yield at the top of the column: 98.4%
but-1-ene in isobutene at the top of the column: 423 ppm.

What is claimed is:

1. A process for processing a feedstock comprising a major amount of olefinic hydrocarbons having 4 carbon atoms per molecule, including isobutene as well as but-1-ene and but-2-enes, wherein the process comprises processing said feedstock in a distillation zone associated with a hydroisomerization reaction zone located at least partly external to the distillation zone, said processing comprising withdrawing at the height of a draw-off level of the distillation zone at least part of the liquid flowing in the distillation zone, passing said liquid into the external hydroisomerization reaction zone to form a hydroisomerized effluent, and reintroducing at least part of the effluent from said reaction zone into the distillation zone at one or more reintroduction level(s), so as to ensure the continuity of the distillation.

2. A process as claimed in claim 1 in which the reintroduction level is located at or adjacent to said draw-off level.

3. A process as claimed in claim 1 in which the reintroduction level is located at a distance from said draw-off level corresponding to a height in the range of 0 to 4 theoretical plates above or below said draw-off level.

4. A process as claimed in claim 1 in which the feedstock is produced from a cut comprising for the major part thereof olefinic hydrocarbons comprising 4 carbon atoms per molecule by treating said cut in a 1st hydroisomerisation zone located upstream of said distillation zone.

5. A process as claimed in claim 4 in which each hydroisomerization zone is such that any hydroisomerization reaction is carried out in the presence of a hydroisomerization catalyst and a gaseous flow comprising hydrogen.

6. A process as claimed in claim 4 in which for the first upstream hydroisomerization zone and for the part of the hydroisomerization zone associated with the distillation zone external to the distillation zone, the pressure of this hydroisomerization stage is in the range of 1 to 40 bars, the temperature is in the range of 20 to 150° C., and the space velocity within said part, calculated in relation to the catalyst, is in the range of from about 1 to 100 $h^{-1}$ (volume of feed per volume of catalyst and per hour).

7. A process as claimed in claim 1 in which the distillation zone is supplied, in addition to the supply of the effluent which constitutes the main feedstock, with a secondary feedstock which is a $C_4$ olefinic cut containing at least isobutene as well as but-1-ene and but-2-enes.

8. A process as claimed in claim 1 further comprising 1 to 6 draw-off level(s).

9. A process as claimed in claim 1 in which distillation is performed at a pressure in the range of 2 to 30 bars, a reflux ratio in the range of 1 to 30, a temperature at the top of the distillation zone in the range of 0 to 200° C. and a temperature at the bottom of the distillation zone in the range of 5 to 250° C.

10. A process as claimed in claim 1 in which hydroisomerization reaction zone associated with the distillation zone is totally external to the distillation zone.

11. A process as claimed in claim 1 in which hydroisomerization zone associated with the distillation zone is both partly incorporated in the distillation zone and partly external to the distillation zone.

12. A process as claimed in claim 1 in which a catalyst bed of the external part of the hydroisomerization zone associated with the distillation zone is fed by at least part of the liquid effluent flowing on a plate of the distillation zone at the draw-off level which plate is used for feeding said bed, and the effluent of said bed is re-injected on a plate located at a distance from said draw-off plate in the range of 0 to 4 theoretical plates.

13. A process as claimed in claim 1 in which the flow rate of a reactor of the external part of the hydroisomerization zone associated with the distillation zone, at the draw-off level which feeds said reactor, is in the range of 0.5 to 1.5 time the flow rate of the liquid effluent flowing on said plate, associated to said draw off level.

14. A process as claimed in claim 1 in which a supported catalyst is used in any hydroisomerization zones, said catalyst comprising at least one noble metal from group VIII selected from the group consisting of ruthenium, rhodium, palladium, osmium, iridium and platinum, or nickel, processed by a sulfur-containing compound, then by hydrogen prior to being used.

* * * * *